United States Patent
Azar et al.

(10) Patent No.: US 6,187,001 B1
(45) Date of Patent: Feb. 13, 2001

(54) APPARATUS AND METHOD FOR REMOVING HAIR

(75) Inventors: Zion Azar, Shoham; Pinchas Shalev, Kfar-Saba, both of (IL)

(73) Assignee: Radiancy Inc., Orangeborg, NY (US)

( * ) Notice: Under 35 U.S.C. 154(b), the term of this patent shall be extended for 0 days.

(21) Appl. No.: 09/220,580

(22) Filed: Dec. 28, 1998

Related U.S. Application Data

(63) Continuation of application No. PCT/IL98/00605, filed on Dec. 14, 1998.

(30) Foreign Application Priority Data

Dec. 31, 1997 (IL) .......................................... 122840

(51) Int. Cl.[7] .................................................. A61B 18/18
(52) U.S. Cl. ................................ 606/9; 606/27; 219/223; 219/226
(58) Field of Search .................................. 606/9–11, 2, 3, 606/13, 27, 28, 32, 36, 43, 131, 133; 219/223, 226, 228, 230, 222, 460.1, 461.1, 534, 535

(56) References Cited

U.S. PATENT DOCUMENTS

| | | |
|---|---|---|
| 3,934,115 | 1/1976 | Peterson . |
| 4,819,669 * | 4/1989 | Politzer . |
| 5,059,192 | 10/1991 | Zaias . |
| 5,405,368 * | 4/1995 | Eckhouse . |
| 5,522,814 * | 6/1996 | Bernaz . |
| 5,595,568 | 1/1997 | Anderson et al. . |
| 5,606,798 * | 3/1997 | Kelman . |
| 5,846,252 * | 12/1998 | Mehl, Sr. . |
| 5,871,480 * | 2/1999 | Tankovich . |
| 5,885,273 * | 3/1999 | Eckhouse et al. . |

FOREIGN PATENT DOCUMENTS

| | | |
|---|---|---|
| 0 736 308 A2 | 10/1996 | (EP) . |
| 0 788 814 A2 | 8/1997 | (EP) . |

* cited by examiner

Primary Examiner—Linda C. M. Dvorak
Assistant Examiner—Bryan K. Yarnell
(74) Attorney, Agent, or Firm—Fenster & Company Patent Attorneys, Ltd.

(57) ABSTRACT

An apparatus and method for removing hairs from a region of skin, the apparatus including:

a housing having an opening therein, the housing forming a cavity enclosing a volume of air when the opening is placed in contact with the region of skin;

a switchable heat source disposed within the housing that rapidly heats the volume of air to a temperature sufficient to destroy the hair by conduction of heat along the length of the hair to a follicle thereof; and a power source that controllably energizes the heat source.

61 Claims, 10 Drawing Sheets

APPARATUS AND METHOD FOR REMOVING HAIR

RELATED APPLICATION

This application is a continuation of PCT Application Number PCT/IL98/00605, filed Dec. 14, 1998, which designates the United Sates of America.

FIELD OF THE INVENTION

The present invention relates to apparatus and methods for hair removal.

BACKGROUND OF THE INVENTION

There are several types of devices for hair removal known in the art. One type includes mechanical devices used by a user to remove hairs by the user himself or herself. These include shavers and other mechanical devices. These mechanical devices are disadvantageous at least in two aspects, namely they remove the hairs for a relatively short time, and in most if not all cases they cause some degree of pain.

Other types of devices are directed to long term hair removal. Electrolysis devices are based on the use of "electric needles". Such fine needles are inserted into the hair follicle and apply an electric current to each hair. The current heats the hair and causes its carbonization and also heats the tissue near the hair causing its coagulation and partial or full coagulation of the blood capillaries which supply blood to the hair follicle. While such devices can result in permanent hair removal, each hair must be treated individually, making hair removal by this method a tedious often painful, time consuming, and expensive.

Another class of devices are Photothermolysis devices which are usually operated by physicians in clinics. These devices are based either on lasers (e.g. Ruby lasers) such as the laser device disclosed in U.S. Pat. No. 5,059,192 to Zaias or an incoherent light source coupled with filters and elaborate electronics to provide pulses of various durations and wave lengths as described in U.S. Pat. No. 5,405,368 and European Patent publications EP 0 788 814 and EP 0 736 308 to Eckhouse. The Eckhouse documents teach heating the hair directly by a high flux of visible radiation that is absorbed by the hair follicles. Various filters and/or pulse lengths are used depending on the depth of penetration desired and the color of the hair being removed.

SUMMARY OF THE INVENTION

One aspect of some preferred embodiments of the invention provides an improved apparatus for hair removal. Some of these embodiments of invention may be used by a user to remove hair from his or her own body.

In a preferred embodiment of the invention, a cavity, is enclosed between a housing and a region of skin. A volume of air is enclosed within the cavity. The volume of air is heated by a fast heating source such as a flash lamp to provide a temperature high enough to kill any hair within the cavity. In a preferred embodiment of the invention, a heat gradient, having a higher temperature at the end of the air volume adjacent the flash lamp and a lower temperature at the end of the air volume adjacent the skin, is formed. The parts of the hairs closer to the flash lamp are heated by the hot air resulting in removal of at least part of the hairs. Alternatively or additionally, the conduction of heat along the hair shafts heats the parts of the hairs sheathed within the hair follicles and the hair follicles which may further assist the hair removal by coagulating the capillary blood vessels supplying the hair follicles. This later heating preferably causes the hair to die, so that there is no regrowth.

In accordance with some preferred embodiments of the invention heating of the hairs and the region of skin underneath the apparatus is terminated at a selected time after flashing the flash lamp to prevent skin overheating. The termination of heating may be achieved by manually lifting the apparatus away from the skin or by automatically pumping air into the cavity at a selected time after the flashing of the flash lamp.

Additionally, the skin and portions of the hair within the follicles may be heated by broad band radiation emitted by the heat source (flash lamp). While this heating is not necessary for hair removal according to the invention, the irradiation may also assist in heating those parts of the hair shafts and the hair follicles and facilitate the heating of hair follicles to the coagulation temperature.

In accordance with preferred embodiments of the invention, means are provided for filtering the radiation to reduce the amount of low wavelength radiation from reaching the skin. Such low wavelength radiation is absorbed by hemoglobin in the blood and may destroy it.

There is thus provided, in accordance with a preferred embodiment of the invention, apparatus for removing hairs from a region of skin, the apparatus comprising:

a housing having an opening therein, the housing forming a cavity enclosing a volume of air when the opening is placed in contact with the region of skin;

a switchable heat source disposed within the housing which rapidly heats the volume of air to a temperature sufficient to destroy the hair by conduction of heat along the length of the hair to a follicle thereof, and a power source which controllably energizes the heat source.

Preferably, the heat source forms a temperature gradient between the source and the skin.

Preferably, the cavity is a sealed cavity.

In a preferred embodiment of the invention, the heat source also provides pulsed light that irradiate the region of skin, the light having an energy insufficient to destroy the hair.

Preferably, the pulsed light is a broad band pulsed light.

Preferably, the apparatus includes a filter disposed between the heat source and the opening which filters a preselected portion of the pulsed broad band light.

In a preferred embodiment of the invention, the heat source is a flash lamp or an arc discharge lamp. Preferably, the flash lamp comprises at least one glass xenon lamp. Preferably, the flash lamp comprises at least one quartz xenon flash lamp. Preferably, the at least one flash lamp comprises at least two lamps in series electrical connection. Preferably, the heat source is disposable.

In a preferred embodiment of the invention, the housing further comprises a sealing gasket attached to the housing along the circumference of the opening.

In a preferred embodiment of the invention, the apparatus includes a pump having a port communicating with the cavity. Preferably, the apparatus a controller that energizes the pump to reducing the air pressure within the air cavity to lift at least some of the hairs from the skin. Preferably, the controller causes energizing of the heat source after lifting at least some of the hair. Preferably the controller energizes the pump to exchange air within the cavity at a predetermined time after the heat source is energized.

In a preferred embodiment of the invention, the apparatus includes at least one valve that allows exchange of air within the cavity when the pump is energized. Preferably, the at least one valve is at least one one-way valve which allows air to enter the cavity when the pump is activated to draw air from the cavity. Alternatively, the pump pumps air into the cavity at the predetermined time.

Preferably, the apparatus includes a hair aligning member situated at the opening which raises at least some of the hairs from the skin. Preferably, the hair aligning member is a flat comb-like member or a flat perforated member. Preferably, the hair aligning member is made of a material which substantially blocks light having a wavelength lower than about 400 nanometers and substantially passes light having a wavelength higher than about 450 nanometers.

Preferably, the apparatus includes a reflector that reflects light produced by the heat source toward the skin. Preferably, the reflector substantially absorbs light having a wavelength lower than 400 nanometers.

In some preferred embodiments of the invention the apparatus includes an extension, the extension having a first end attachable to the opening and a second end placeable on the region of skin, the extension has an aperture therethrough defining an area for removing hairs.

Preferably, the housing is made of a heat insulating material.

In preferred embodiments of the invention, the power source is an electrical power source.

In preferred embodiments of the invention the apparatus fits into the palm of a hand.

There is further provided, in accordance with a preferred embodiment of the invention, apparatus for removing hairs from a region of skin, the apparatus comprising:

a housing having an opening therein, the housing forming a cavity enclosing a volume of air when the opening is placed in contact with the region of skin;

a switchable energy source disposed within the housing which provides energy in an amount sufficient to destroy at least some of the hairs;

a power source that controllably energizes the heat source; and a pump having a port communicating with the cavity.

Preferably, the apparatus includes a controller that energizes the pump to reducing the air pressure within the air cavity to lift at least some of the hairs from the skin. Preferably, the controller causes energizing of the energy source after lifting at least some of the hair. Preferably, the controller energizes the pump to exchange air within the cavity at a predetermined time after the energy source is energized. Preferably, the apparatus includes at least one valve that allows exchange of air within the cavity when the pump is energized. Preferably the at least one valve is at least one one-way valve which allows air to enter the cavity when the pump is activated to draw air from the cavity. Preferably, the pump pumps air into the cavity at the predetermined time.

There is further provided, in accordance with a preferred embodiment of the invention, a method for removing a plurality of hairs from a region of skin, each of the hairs having a first part disposed in a hair follicle within the skin and a second part distal of the skin, the method comprising:

selectively heating a portion of the second part of at least one of the plurality of hairs;

conducting heat from the second part to the hair follicle of the at least one of the plurality of hairs to thereby heat the hair follicle to a temperature high enough to cause the coagulation of the blood vessels supplying blood to the hair follicle.

Preferably, the method includes, prior to selectively heating:

irradiating the region of skin with a pulse of light to elevate the temperature of the first part of at least some of the hairs and of hair follicles of the at least some of the hairs to a first temperature, the first temperature being lower than the coagulation temperature of blood.

Preferably, the pulse of light is a broad band pulse of light. Preferably, the pulse of light is filtered to remove a preselected portion of the pulsed broad band light.

Preferably, the method includes keeping the temperature of the region of skin away from the hairs below the temperature required to coagulate blood.

In a preferred embodiment of the invention. selectively heating comprises:

providing a temperature gradient such that air in the vicinity of the second portion of the at least one hair is at a high temperature and air in the vicinity of the skin is below the temperature required to coagulate blood, except for heating of the immediate vicinity of the hair by conduction via the hair.

Preferably, selectively heating comprises flashing a flash lamp or an arc discharge lamp at a distance from the skin.

Preferably, selectively heating comprises:

providing a cavity overlying the region of skin, the cavity comprising a volume of air having a first end proximal to the region of skin and a second end distal to the region of skin;

heating the air in the cavity to create a temperature gradient in the volume of air, the temperature gradient having a first temperature at the first end and a second temperature at the second end, the first temperature being lower than the second temperature; and maintaining the temperature gradient for a predetermined time interval sufficient for heating at least some of the plurality of hairs extending within the volume of air to a temperature sufficient to remove at least part of at least some of the plurality of hairs, while keeping the first temperature below the coagulation temperature of the region of skin.

There is further provided, in accordance with a preferred embodiment of the invention, a method for removing hairs from a region of skin, the region of skin having a plurality of hairs, each of the plurality of hairs includes a first part disposed in a hair follicle within the region of skin and a second part distal of the region of skin, the method comprising:

providing a cavity overlying the region of skin, the cavity comprising a volume of air having a first end proximal to the region of skin and a second end distal to the region of skin;

heating the air in the cavity to create a temperature gradient in the volume of air, the temperature gradient having a first temperature at the first end and a second temperature at the second end, the first temperature being lower than the second temperature; and maintaining the temperature gradient for a predetermined time interval sufficient for heating at least some of the plurality of hairs extending within the volume of air to a temperature sufficient to remove at least part of at least some of the plurality of hairs, while keeping the first temperature below the coagulation temperature of the region of skin.

Preferably, the air cavity is a sealed air cavity.

Preferably, the method includes removing heat from the air after maintaining the temperature gradient, so as to keep the temperature of the skin below the coagulation temperature. Preferably, removing heat comprises cooling the air in the cavity. Preferably, cooling the air comprises removing air from the cavity.

In preferred embodiments of the invention, heating comprises providing a pulsed discharge.

Preferably the method includes heating the skin and the first part of the hair to a temperature below the coagulation temperature using electromagnetic radiation. Preferably, heating the skin and the first part of the hair includes filtering electromagnetic radiation to produce a pulse of non-coherent, narrow band electromagnetic energy.

Preferably, heating comprises pulsing a flash lamp or an arc discharge lamp.

There is further provided, in accordance with a preferred embodiment of the invention, a method for removing hair by a person comprising:

applying heat from a portable hand held apparatus for hair removal, the apparatus comprising a housing having an opening, a switchable heat source disposed within the housing and a power source that energizes the heat source, characterized in that the heat generates a temperature gradient in an air volume enclosed in a cavity formed by placing the opening on a region of skin, the temperature gradient being suitable for hair removal.

Preferably applying of heat is performed by the person on his own skin.

The method preferably includes manually removing the opening of the housing from the region of skin.

There is further provided, in accordance with a preferred embodiment of the invention a method for hair removal by oneself comprising:

applying a heat pulse suitable for hair removal from a portable hand held apparatus, the applying performed by the person on his or her own skin.

BRIEF DESCRIPTION OF THE DRAWINGS

The invention will be more clearly understood by the following description of nonlimiting preferred embodiments of preferred embodiments of the invention described, with reference to the accompanying drawings, in which like components are designated by like reference numerals, and wherein.

DETAILED DESCRIPTION OF THE INVENTION

Figure 1:
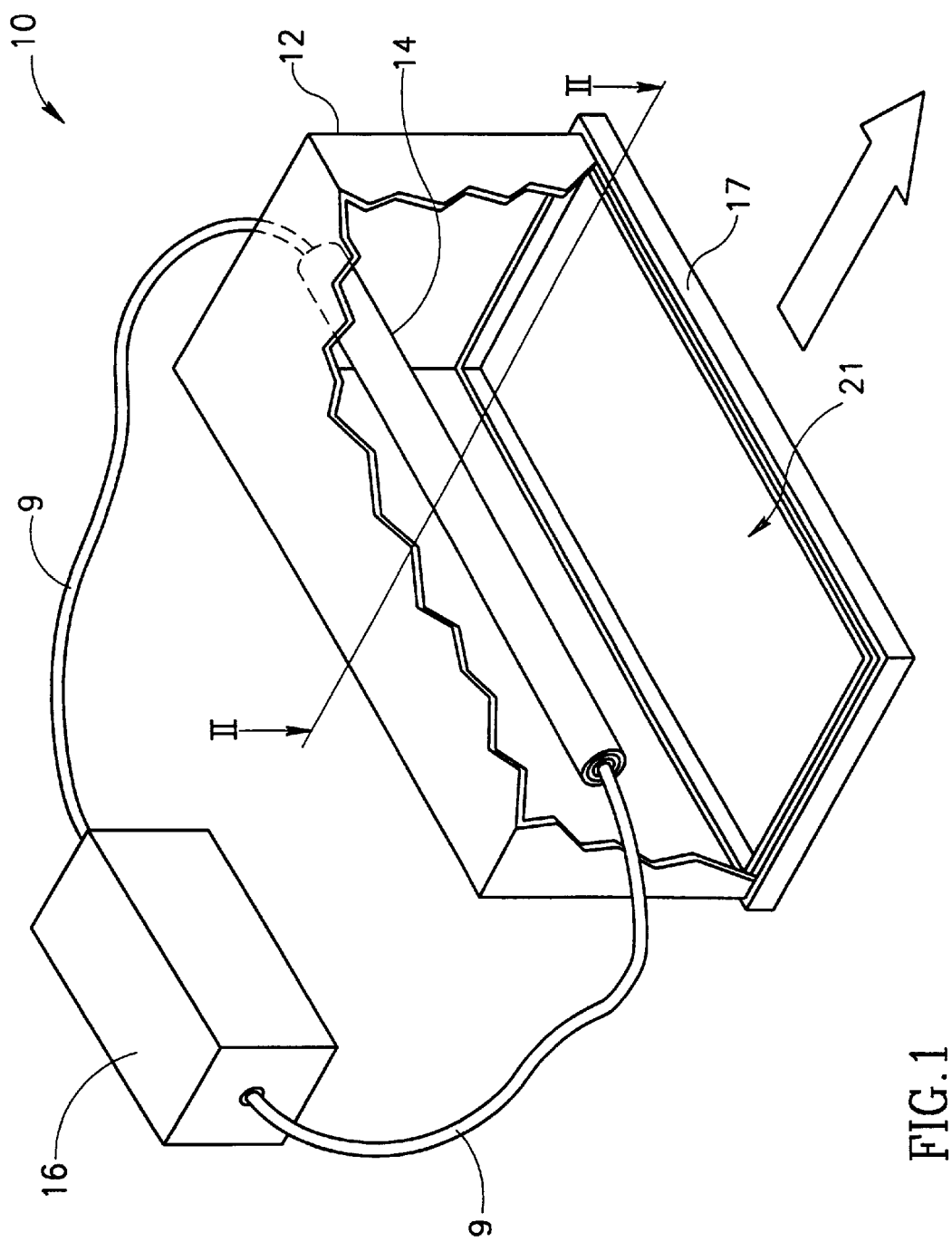
FIG. 1 is a perspective breakaway view illustrating a portable hand held device for hair removal in accordance with one preferred embodiment of the present invention.
Figure 2:
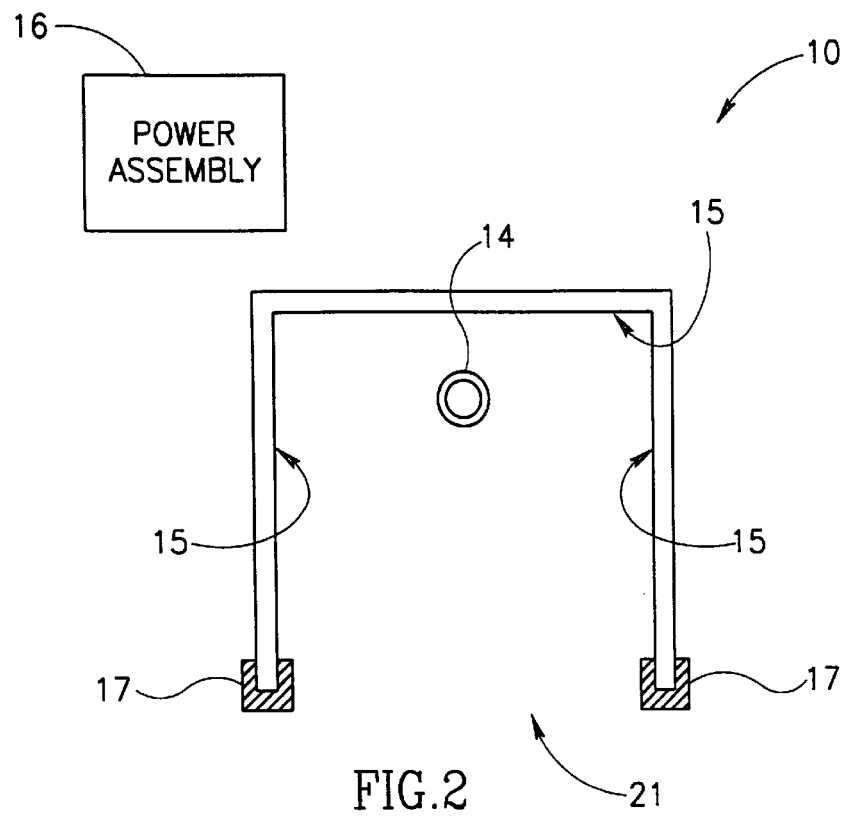
FIG. 2 is a cross section illustration of the device of FIG. 1.

Reference is now made to FIG. 1 which is a pictorial illustration of a portable hand held device for hair removal, generally referenced 10, constructed and operative in accordance with an embodiment of the present invention and to FIG. 2 which is a cross section illustration of the device 10 of FIG. 1 taken along the lines II—II. Device 10 includes a housing 12, a flash lamp 14 for providing heat and a pulsed broad band light suitable for hair removal, and an assembly 16 for supplying power for energizing and controlling the application of power to flash lamp 14. Flash lamp 14 can be a xenon flash lamp having a glass tube, but can also be any other suitable flash lamp. Assembly 16 is preferably electrically connected to flash lamp 14 by electrically conducting insulated wires 9. For the sake of clarity of illustration, wires 9 are not shown in FIG. 2. Housing 12 of device 10 has an opening 21 therein.

Housing 12 is preferably made of a thermally insulating material, for example, a high temperature plastic or a ceramic material. Housing 12 preferably has a sealing gasket 17 made from any suitable flexible material such as soft rubber for sealing the contact between housing 12 and a skin surface (not shown) on which opening 21 of housing 12 is placed before and during depilation. However, sealing gasket 17 is not critical to the operation of device 10. However, it is desirable that sealing be achieved by pressing opening 21 against the skin.

Housing 12 includes internal surfaces 15 that may be coated with a diffusely reflective coating (not shown) of high reflectivity such as a finely divided titanium dioxide based coating or any other suitable heat resistant highly reflective coating. As described below, coating that reflect IR well but do not reflect radiation having long wavelengths may advantageously be used.

Figure 3:
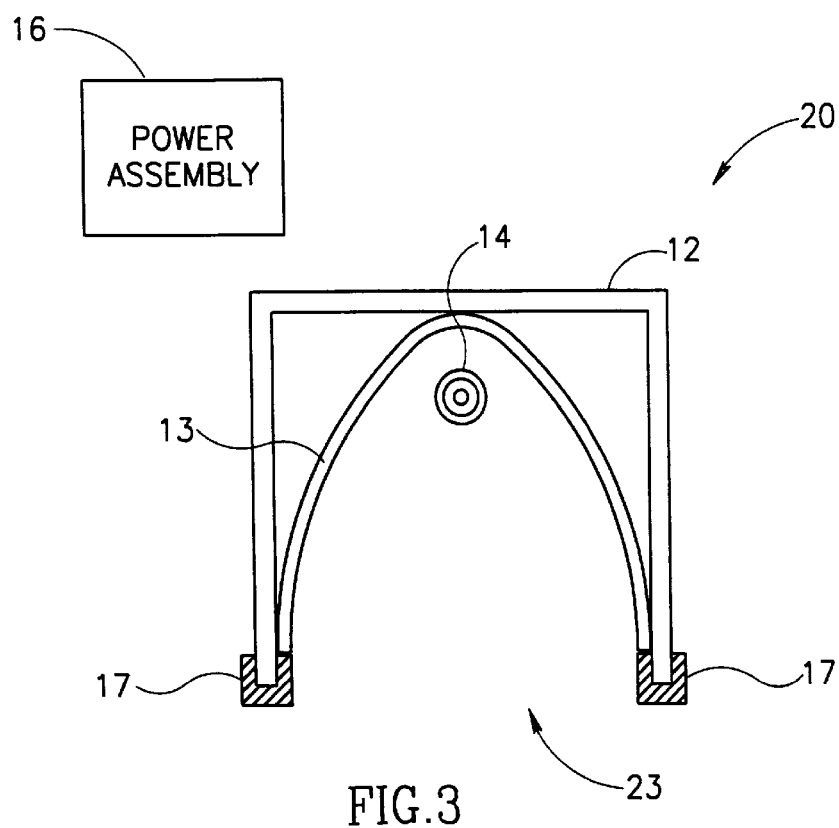
FIG. 3 is a cross section illustrating another implementation of the portable hand held device for hair removal, in accordance with another preferred embodiment of the present invention.

Reference is now made to FIG. 3 which is a cross section illustrating another implementation of a portable hand held device 20 for hair removal, in accordance with another preferred embodiment of the present invention. Device 20 is similar to device 10 except that it includes a reflector 13 within housing 12. Flash lamp 14 is disposed within reflector 13. For the sake of clarity of illustration, wires 9 between the flash lamp 14 and the assembly 16 are not shown in FIG. 3. Housing 12 of device 20 has an opening 23 therein, having the function of opening 21 of device 10.

Figure 4:
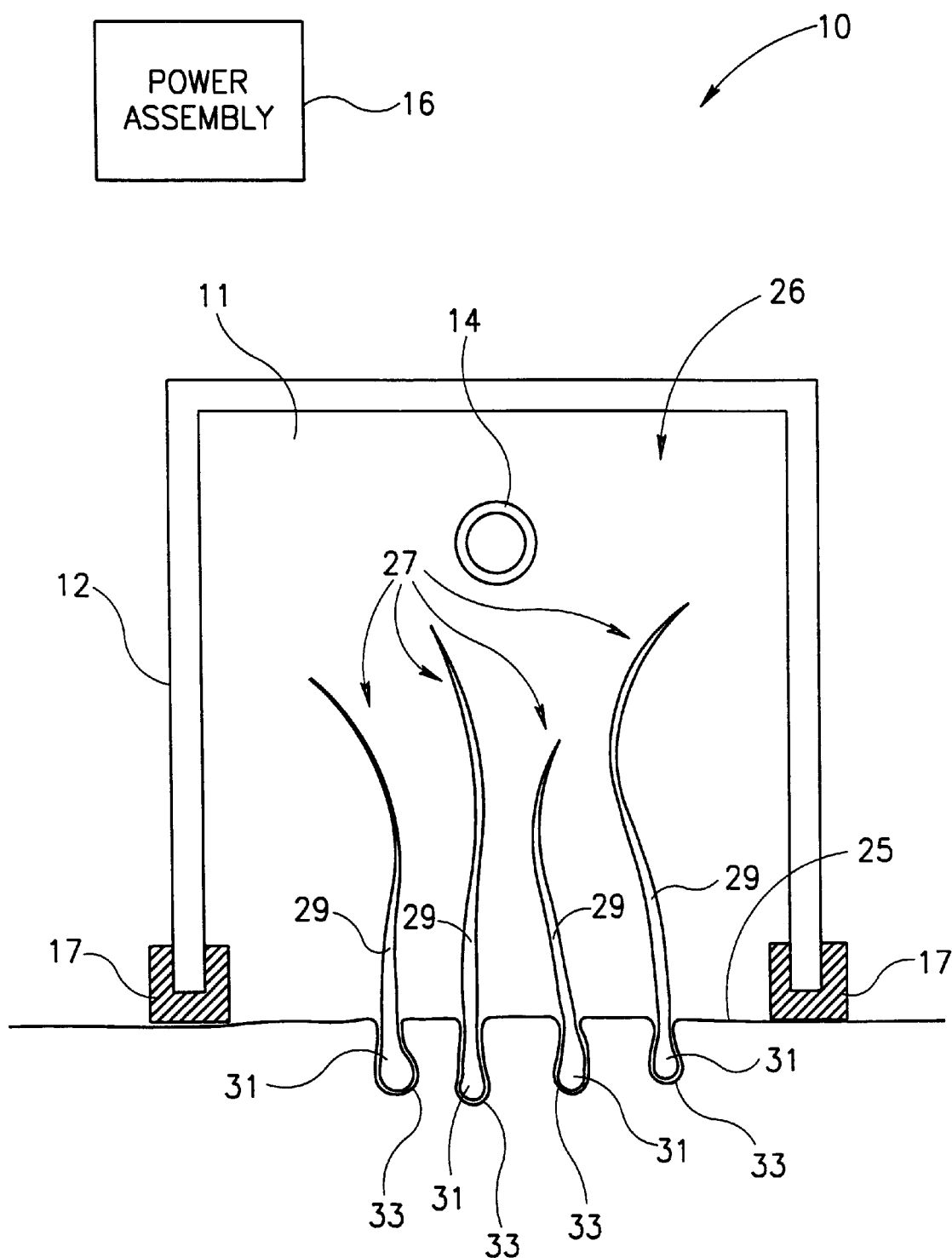
FIG. 4 is a schematic cross section illustration useful in understanding the method of operation of the device of FIGS. 1 and 2, in accordance with a preferred embodiment of the invention.

Reference is now made to FIG. 4 which is a schematic cross section illustration useful in understanding the method of operation of the device of FIG. 2.

When opening 21 of device 10 is placed on skin 25, a sealed air cavity 11 is formed between housing 12 and skin 25. Sealed air cavity 11 contains a volume of air 26. Sealing of the cavity is desirable and is preferably achieved by pressing gasket 17 against skin 25.

The region of skin 25 covered by opening 21 includes a plurality of hairs 27. Each of hairs 27 has a first part 31 which is disposed within hair follicles 33 and a second part 29 protruding outside of skin 25 in a direction generally distal from the surface of skin 25.

A user activates device 10 by energizing flash lamp 14. For example, device 10 may be activated by the user by pressing a button (not shown) or activating a switch (not shown) positioned on assembly 16 or on any other suitable part of the device 10. When assembly 16 energizes flash lamp 14, flash lamp 14 produces a broad band light pulse having an approximate duration of 1–75 milliseconds and an energy density of preferably between 1.5 to 5 Joule/cm$^2$ measured on the skin.

The light pulse irradiates the region of skin 25 underlying opening 21 of housing 12. The light pulse also irradiates hairs 27. A part of the light pulse is absorbed by melanin pigment in hairs 27. Another smaller part of the light pulse is absorbed by the region of the skin 25 directly underneath the opening 21. In preferred embodiments of the invention, the amount of energy pulsed through the flash lamp 14 is such that the absorption of the light by the region of skin 25 raises the temperature of the region of skin 25. However, this temperature is preferably lower than the coagulation temperature of blood. Preferably, the temperature of hair follicles 33 and skin 25 due to the absorption of radiation from the light pulse should not exceed 50–65° C. Since most of the radiation from flash lamp 14 is absorbed by the melanin in the hair while only a small portion of the radiation is absorbed by the skin tissue, skin tissue which is more than about 0.2 mm from hair follicles 33 is heated negligibly.

About half of the electrical energy used to energize flash lamp 14 is wasted to heat the flash lamp itself, heating flash lamp 14 to a much higher temperature than that of air volume 26 surrounding the flash lamp 14. Typically, in glass flash lamps the temperature of the flash lamp may reach a temperature between 600–800° C. and in quartz flash lamps the temperature of the flash lamp may reach a temperature between 1200–1600° C. The maximal temperature of the flash lamp is typically reached within 1–2 milliseconds.

The air immediately adjacent to the flash lamp 14 is heated by the flash lamp. Heat is conducted by convection from air adjacent flash lamp 14 to air which is further away from flash lamp 14, creating a temperature gradient in the air contained in cavity 11.

The temperature of the air close to the flash lamp will be the highest and will decrease as the distance from flash lamp 14 increases. Since each of hairs 27 protrudes from skin 25 along the sealed air cavity 11 in the general direction of the flash lamp 14, those parts of hairs 27 that are closer to flash lamp 14 will be exposed to air having a higher temperature than the parts of the same hairs which are closer to skin 25. Thus, the part of a hair 27 closer to the flash lamp will be heated by the hot air to a higher temperature than the part of the same hair which are closer to skin 25. Heat will be conducted from the hotter parts of hair 27 towards first part 31 of hair 27. The heat flow will increase the temperature of first part 31 and hair follicle 33 surrounding it to a temperature of approximately 70–100° C. which is sufficient to cause the coagulation of the blood capillaries supplying blood to hair follicle 33.

Additionally, the temperature reached by many of the hairs at parts which are closer to the flash lamp are sufficiently high to cause burning or carbonization of a substantial portion of the hair thus effectively removing a substantial portion of the hair.

It is noted that, it is not necessary to shave hairs 27 prior to hair removal by the methods of the present invention. However, if the hair is cut, shaved or otherwise shortened, It was found that hairs that have a shaft protruding roughly 2 mm or more from the skin surface in the general direction towards flash lamp 14 are removed more effectively by the device.

The heat gradient in the volume of air 26 within air cavity 11 tends to equilibrate so that the air temperature near the surface of the region of skin 25 rises with time after the energizing of flash lamp 14. To prevent the temperature of the skin from rising above 70° C., housing 12 may be lifted away from skin 25. Lifting of housing 12 causes opening of air cavity 11 and prevents excess heating of the skin 25 allowing air at room temperature to contact the skin. Alternatively or additionally, the heated air may be removed from the cavity.

It is noted that, typically, hairs 27 are not necessarily aligned perpendicularly to the surface of the skin. Hairs which are lying in a general direction parallel to the surface of the skin 25 will reach a temperature lower than hairs which are generally aligned perpendicular to the surface of the skin. Thus, it may be desirable to align as many of hairs 27 as possible in a direction generally perpendicular to the surface of the skin.

Figure 5A:
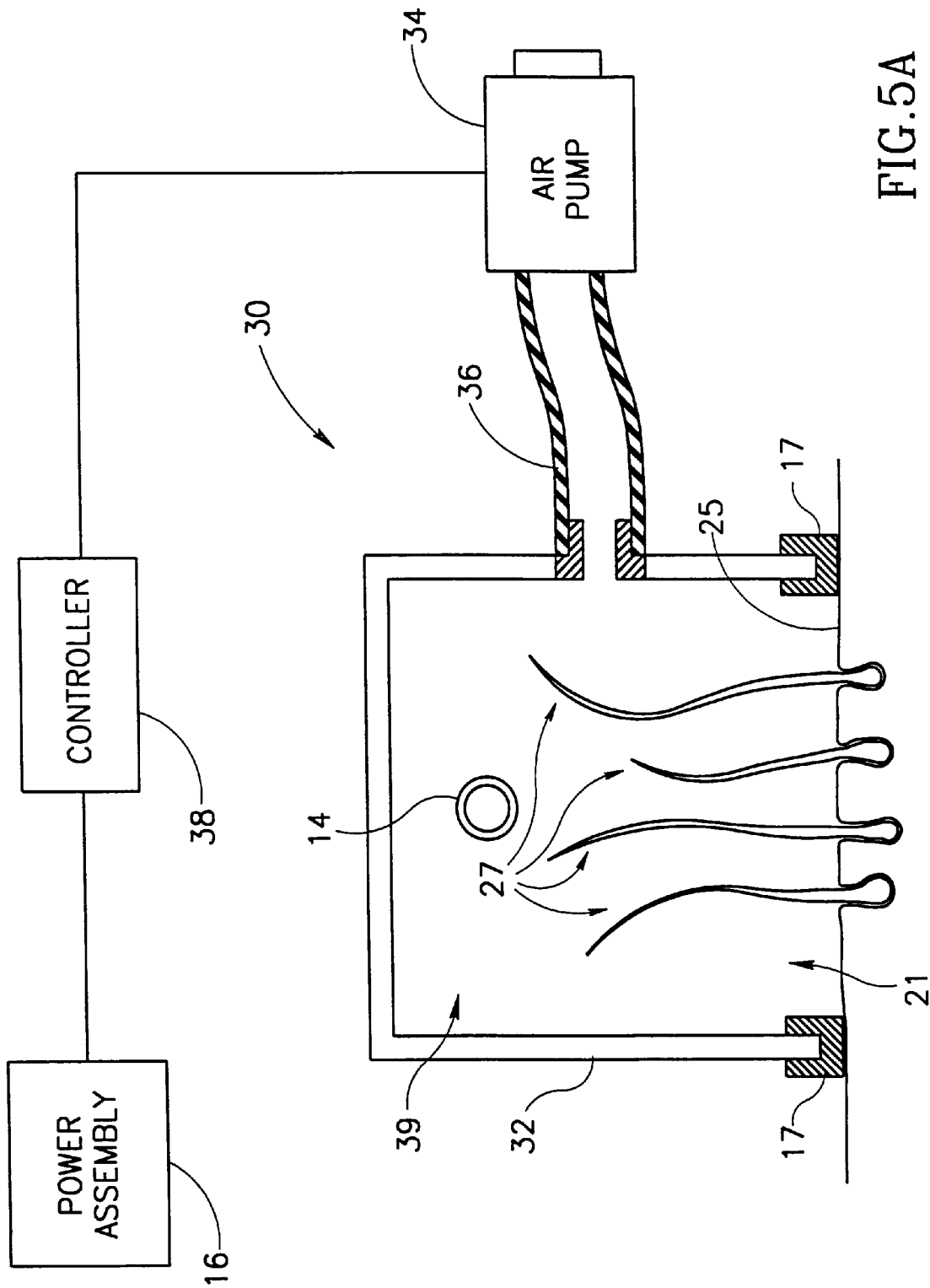
FIGS. 5A and 5B are schematic part cross-sectional partly functional diagrams illustrating portable hand held devices for hair removal, including an air pump for assisting the proper alignment of hairs in accordance with preferred embodiments of the present invention.

Reference is now made to FIG. 5A which is a schematic partly cross-sectional partly functional diagram illustrating a portable hand held device 30 for hair removal, having an air pump 34 for assisting the proper alignment of hairs in accordance with a preferred embodiment of the present invention. Device 30 includes a flash lamp 14 disposed within a housing 32 and an assembly 16 for energizing the lamp 14. Housing 32 has an opening 21 and differs from housing 12 of FIG. 1 in that it is connected to air pump 34, for example by a tube 36. Air pump 36 is preferably an electrical air pump but can be any other suitable small air pump.

Device 30 further preferably includes a controller 38 suitably connected to air pump 36 and to e assembly 16. Controller controls the timing of activation of air pump 36 and the timing of the energizing of flash lamp 14 by assembly 16. Controller 38 may also include a power source (not shown) for supplying power to air pump 36. The power source may be an electrical battery, a mains operated power supply or any other suitable power source. Alternatively, the power to operate air pump 36 may be supplied by a power source (not shown) included within assembly 16 and also used for energizing flash lamp 14. Air pump 36 is preferably a reversible air pump. Reversing the direction of pumping respectively reverses the flow of air into and out of the cavity.

Device 30 is operated by placing opening 21 of the housing 32 on a region of skin 25 to be depilated and activating controller 38. In a preferred embodiment of the invention, controller 38 first activates air pump 36 to pump some of the air out of a sealed air cavity 39 formed between housing 32 and the region of skin 25 adjacent opening 21. The pumping action causes the erection of at least some of hairs 27 so that they do not lie against the skin by applying a gentle suction action to the region. This first action of the pump is desirable, but not essential for operation of the device.

After partial alignment of the hairs is achieved, the pump is preferably turned off and controller 38 activates assembly 16 to energize flash lamp 14. The light and heat pulse generated by flash lamp 14 operate to remove at least part of the hairs 27 as disclosed above in detail for the device 10 of FIG. 1. After the hair removing action is achieved and before the temperature of the region of skin 25 exceeds a value that might cause a skin burn (which is roughly 0.5 seconds after energizing flash lamp 14), controller 38 automatically reverses the direction of air pumping by air pump 36. This reversal pumps air at room temperature from outside of the device 30 into the housing 32, dissipates the heat within the housing by displacing the volume of air within it with air at room temperature. The flow of air also cools the region of skin 25 to prevent the development of a skin burn.

Figure 5B:
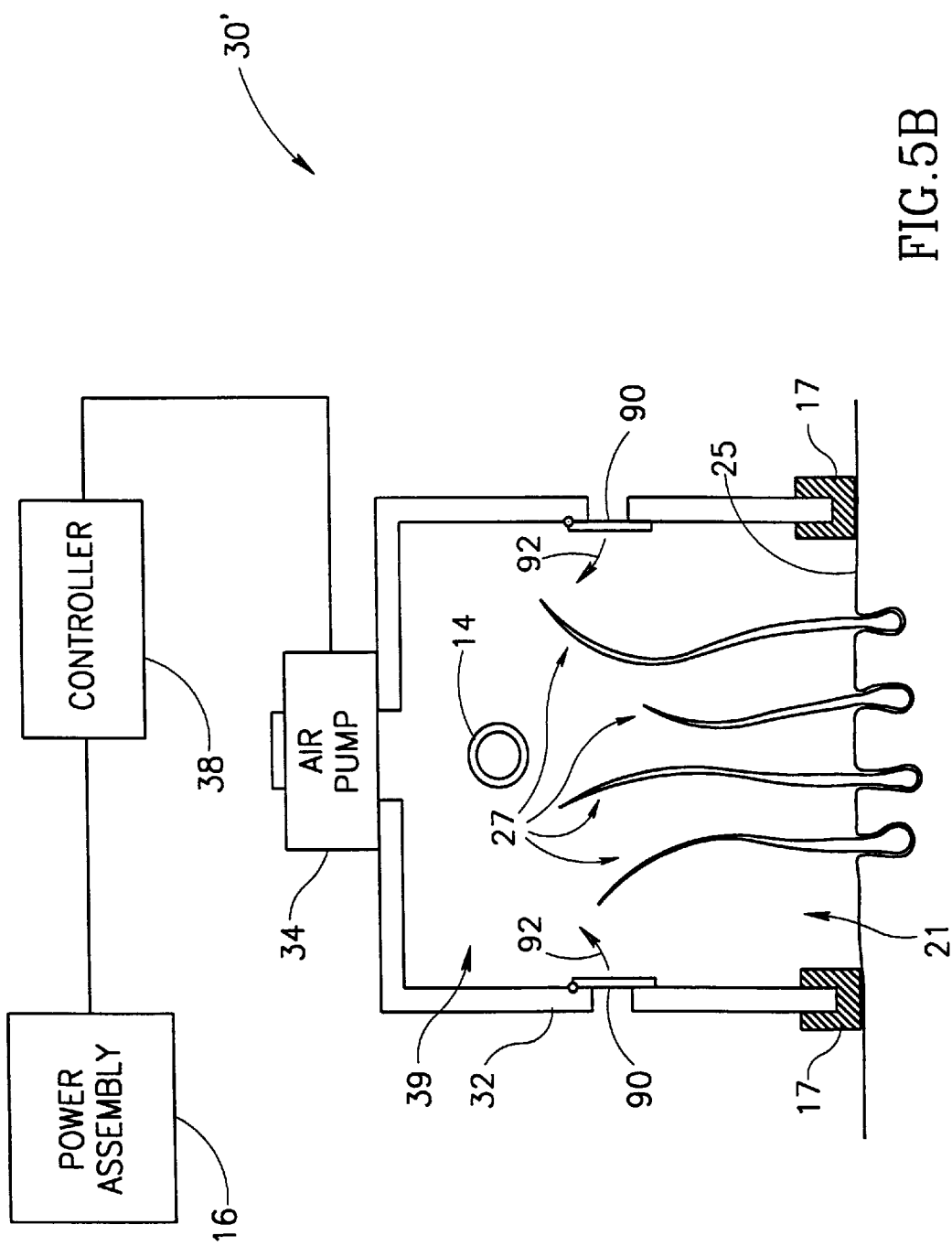

FIG. 5B shows a hair removal device 30' in accordance with an alternative preferred embodiment of the invention. While suction is shown as being applied at the side of the cavity in FIG. 5A, it is more effectively applied at or near the top of the housing, as shown in FIG. 5B. Furthermore, while, as shown in FIG. 5A, the hot air must leave the housing via opening 21, valved openings 90 (which open in direction 92) are provided on the side walls of the housing in FIG. 5B to aid in the entry of fresh air into the cavity and removal of air from the cavity by pump 36. In this embodiment, pump 36 is preferably a purely suction pump. In operation the pump is preferably activated before the flash to raise the hair from the skin. Then the pump operation is interrupted and the lamp is flashed. After a short time the pump is activated again to bring fresh air into the cavity and remove heat from the cavity and from the flash lamp. The time between the flashing of the lamp is such that the hair has enough time to conduct the heat to the follicle and heat it to the proper temperature for coagulation but not so long that the heat from the lamp reaches the skin to the extent that it causes burning or even, preferably, any discomfort. This time is in the order of 0.1–2 seconds, more preferably 0.2–1 seconds and most preferably about 0.5 seconds. It should be noted that the valves are kept closed immediately after flashing by the pressure build-up of the heat in the cavity.

Devices 30 and 30' have the advantage of improving the efficiency of hair removal by improving the hair alignment and also has the advantage of being automatic obviating the need of timely manual lifting of the device by the user.

Figure 6A:
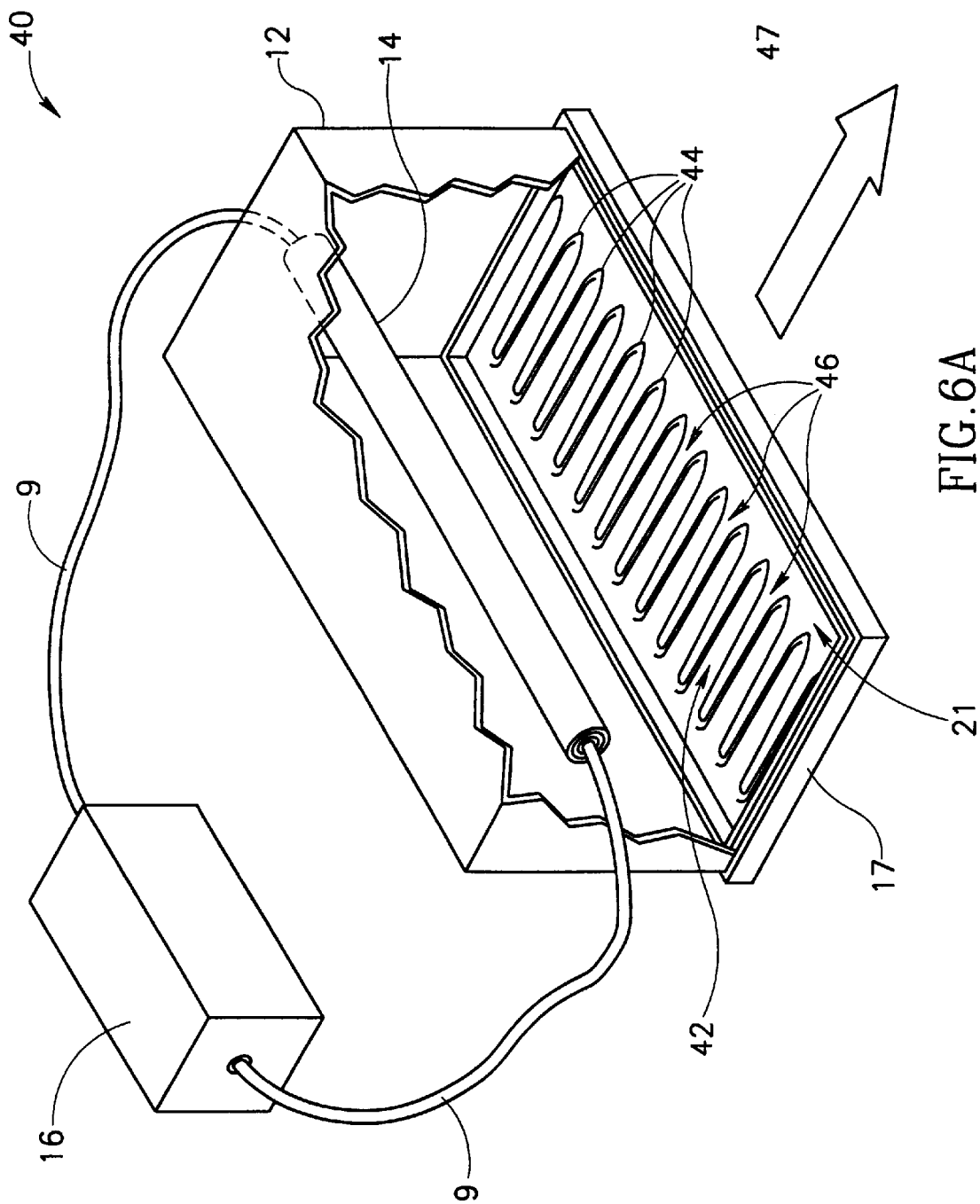
FIG. 6A is a perspective breakaway view illustrating a hair removal device having a comb like hair aligning member for alignment of hairs, in accordance with another preferred embodiment of the present invention.
Figure 6B:
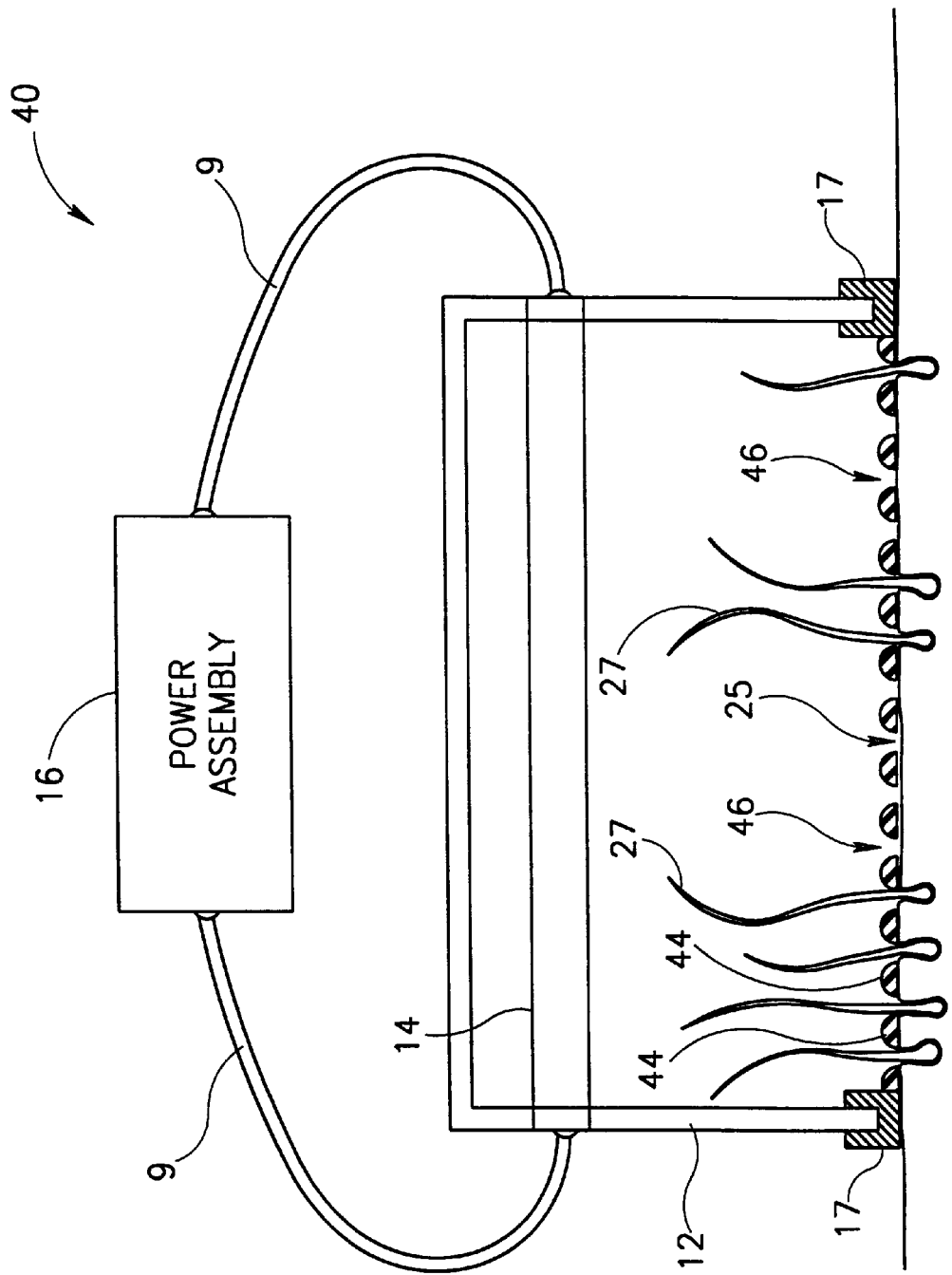
FIG. 6B is a schematic cross section illustration useful in understanding the hair aligning action of the aligning member of the device of FIG. 6A.

Additional methods of hair alignment are also possible. Reference is now made to FIGS. 6A and 6B. FIG. 6A is a schematic perspective breakaway view of a hair removal device 40 having a comb like hair aligning member 42 for hair alignment, in accordance with another preferred embodiment of the present invention.

Device 40 is similar to device 10 of FIG. 1 except that device 40 includes hair aligning member 42 spanning across part of opening 21. Preferably, hair aligning member 42 is a flat thin comb-like member made from a metal such as stainless steel or from any other suitable material such as another metal, plastic, a ceramic material and the like. In a preferred embodiment of the invention hair aligning member 42 includes a plurality of teeth 44 separated by a plurality of narrow gaps 46. Typically, the width of the teeth 44 is approximately 0.7 millimeters and the width of the gaps 66 is approximately 0.2 millimeters. However, these dimensions may be varied to accommodate different hair thicknesses. Furthermore, the hair aligning member 42 may be detachably attached to the housing 12 to facilitate quick attachment of various differently shaped hair aligning members (not shown) by the user.

Hair aligning member 42 may be attached to housing 12 such that when sealing gasket 17 is placed in contact with the skin, teeth 44 contact the skin. Alternatively, hair aligning member 42 may be attached to housing 12 such that when sealing gasket 17 is placed in contact with the skin, teeth 44 do not contact the skin and are positioned a small distance above the skin.

When device 40 is used for removing hair it is placed on the skin so that sealing gasket 17 contacts the skin. Device 40 is moved along the skin in a direction parallel to the orientation of teeth 44 as indicated by an arrow 47. This movement of device 40 along the skin causes some of the hairs (not shown) to enter gaps 44 and improves their alignment in a direction roughly perpendicular to the surface of the skin.

After hair alignment, device 40 (whose internal structure may differ from that shown in FIG. 6A and may have features shown in other FIGS.) is operated to remove hair as disclosed above. These actions of hair aligning followed by hair removing may be then repeated by the user either of the same skin area or on a different skin area.

FIG. 6B is a schematic cross sectional view illustrating of device 40 of FIG. 6A positioned over a region of skin 25. Some of hairs 27 are shown disposed in gaps 46 between different pairs of teeth 44. When device 40 in moved along the skin, comb like member 42 aligns and raises some of hairs 27 to facilitate hair removal.

It is noted that while hair aligning member 42 is shaped like a comb, other implementations of the hair removal device may have other different forms of hair aligning members. For example, the hair aligning members may be constructed in the shape of flat flexible perforated metal sheets (not shown) having a plurality of openings therethrough such as the hair aligning members known in the art and used in electrical shaving machines. The construction of such aligning members is well known to those skilled in the art and will therefore not be further described.

It is further noted that, the methods of hair removal disclosed hereinabove may also be applied to skin without including the first step of photothermal heating of the hair portions within the follicles to a temperature of between 50–65° C. as described above. While the selective heating of the hairs and hair follicles to a sub-coagulation temperature may improve the efficiency of hair removal, hairs can also be removed by the air heating action and subsequent burning and/or carbonization of the hairs caused by the heating of the hair shafts due to the hot air within the sealed air cavity. Thus, hair can still be efficiently removed even in situations where the broad band light pulse from the flash lamp 14 does not efficiently reach the part of the hair shaft which is sheathed within the hair follicle because of partial or full blocking of the light pulse by the hair aligning member 42 or by other different forms of hair aligning members used in different embodiments of the present invention.

It is still further noted that while the preferred embodiments of the hair removing device disclosed above are implemented using a glass xenon flash lamp, the life span of the flash lamp may be significantly improved by using a quartz xenon flash lamp. However, unlike the light generated by glass xenon flash lamps which does not include substantial ultraviolet (UV) radiation (due to the absorbence of UV radiation by the glass tube of the xenon flash lamp), the light generated by quartz xenon flash lamps includes UV light radiation in the spectral range between 200–400 nanometers that may cause damage to the skin tissue. When such quartz flash lamps are used, the light pulsed from the flash lamp has to be filtered to remove the undesirable portion of the UV radiation from the light reaching the skin. For example, if a comb member as shown in FIGS. 6A and 6B is used, it may be made of orange or red colored perspex which blocks at least part of such light.

Figure 7:
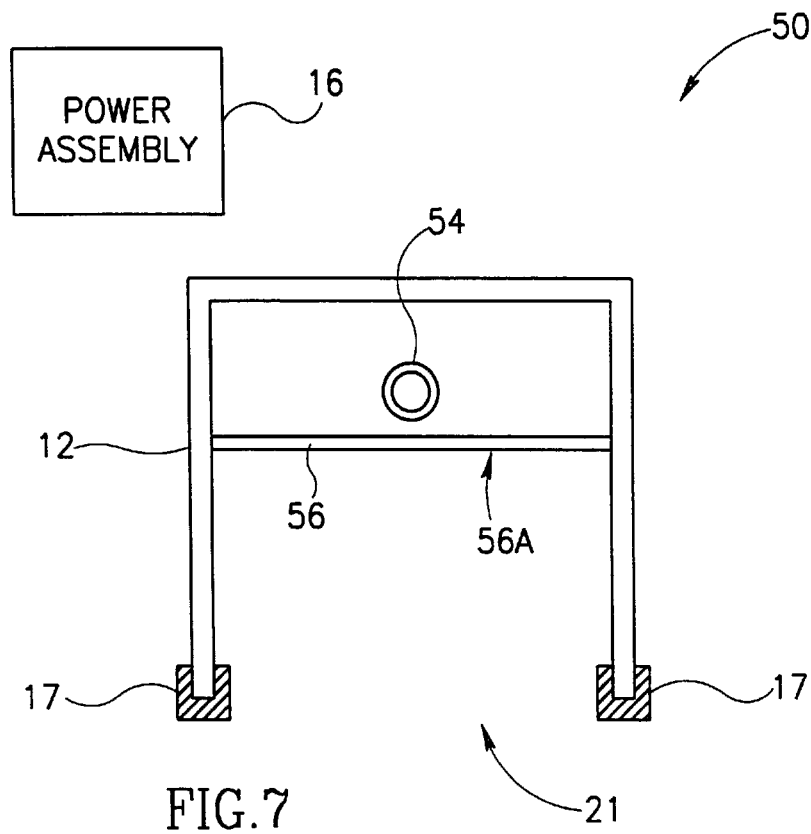
FIGS. 7 and 8 are schematic cross-sectional views of hair removal devices using a quartz flash lamp and different forms of filters for filtering the light pulse, in accordance with additional preferred embodiments of the present invention.
Figure 8:
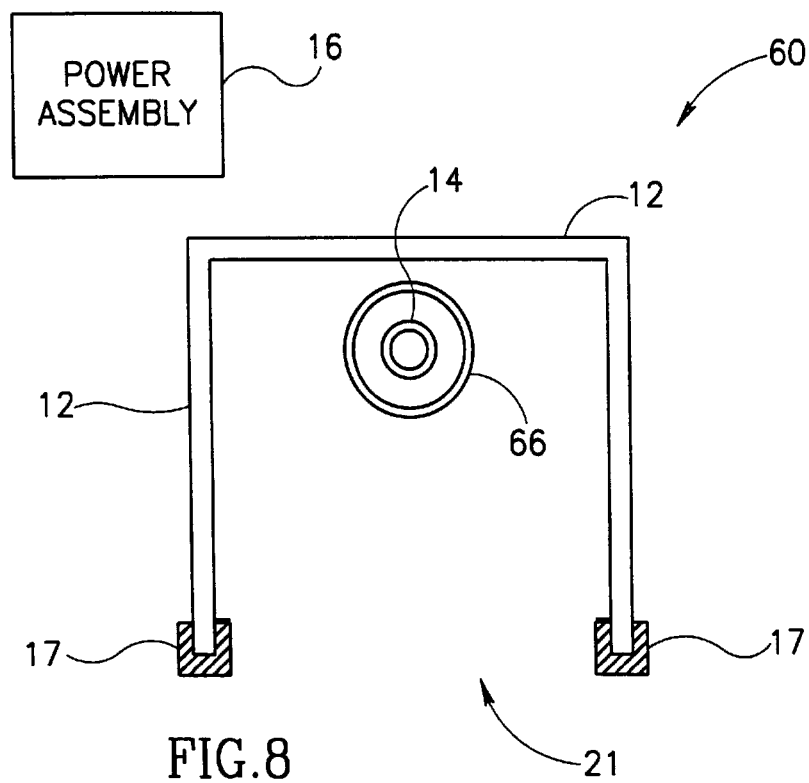

Reference is now made to FIGS. 7 and 8 which are schematic cross-sectional views of hair removal devices using different forms of filters for filtering the light pulse, in accordance with additional preferred embodiments of the present invention.

FIG. 7 illustrates a hair removal device 50. Device 50 is similar to device 10 of FIGS. 1 and 2, except that device 50 uses a quartz flash lamp 54 instead of glass flash lamp 14 of device 10 and includes a filter 56 for filtering out the undesired UV radiation emitted by quartz flash lamp 54. Filter 56 can be a model 450FH90-25 long wave pass filter commercially available from Andover Corporation, NH, USA or merely a colored plastic. This long wave pass filter absorbs most of the radiation having a wavelength below 450 nanometers while transmitting most of the radiation having a wavelength above 450 nanometers.

Filter 56 may be any other suitable filter having the proper absorption properties to absorb the undesirable UV radiation while passing longer wavelengths of radiation, and having a sufficiently high thermal conductivity and a sufficiently low thermal mass to assure a high rate of heat flow from flash lamp 54 and the hot air surrounding it to filter 56 and the subsequent heat flow from filter 56 to air adjacent side 56A of filter 56 facing towards the opening 21. Device 50 is used for hair removal as described above for device 10 except that the heat generated by pulsing the flash lamp 54 has to flow through UV filter 56 to form a temperature gradient in the sealed air cavity enclosed within filter 56, the walls of housing 12 and the skin on which the device 50 is placed.

It is noted that quartz xenon flash lamps may reach an initial temperature of 1200 –1600° C. after pulsing. These temperatures which are higher than those attained by glass xenon flash lamps may compensate for the presence of filter 56.

It is further noted that, while filter 56 of FIG. 7 is flat, filter 56 may have other suitable shapes and geometry. For example, filter 56 may be concave or convex.

FIG. 8 illustrates a hair removal device 60 which is similar to the device 50, except that instead of the flat filter 54 of FIG. 7 device 60 includes a cylindrical filter 66 attached to housing 12. Quartz flash lamp 54 is disposed within cylindrical filter 66 for filtering the broad band light generated by the flash lamp 54 as disclosed above.

As indicated above, the use of a comb with filtration properties may obviate the need for an additional filter.

The devices disclosed above may be used for removing hair from various body regions of the user such as the hands, legs face and other body regions. It is therefore desirable to provide the device of the present invention with a way of adapting the device for removing hair from body regions having different sizes and shapes.

Figure 9:
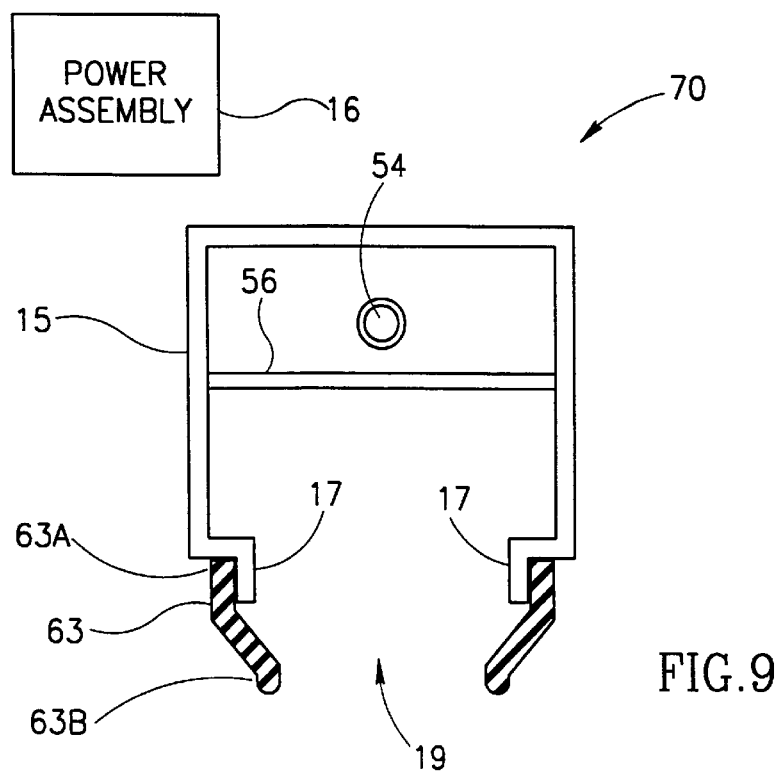
FIG. 9 is a schematic cross section illustrating a device for hair removal adapted for use with a plurality of differently shaped extenders, in accordance with yet another preferred embodiment of the present invention.

Reference is now made to FIG. 9, which is a schematic cross section illustrating a device for hair removal 70 adapted for use with a plurality of differently shaped extenders, in accordance with a preferred embodiment of the invention. Device 70 includes a housing 15 having a raised collar 17. Device 70 further includes a quartz flash lamp 54 and an assembly 16 for energizing flash lamp 54 and for controlling the operation as disclosed above. Device 70 also includes a UV filter 56 attached to housing 15 as disclosed above. An extender 63 is detachably attached to housing 17. In a preferred embodiment of the invention extender 63 is attached to housing 15 by forcing the extender over raised collar 17.

Extender 63 is a preferably hollow and has a first end 63A attachable to the raised collar 17 and a second end 63B for contacting the skin. Extender 63 preferably has an aperture 19 defining an area for removing hairs. In one embodiment of the invention, extender 63 is a metal extender. However, extender 63 is desirably made of a thermally insulating material such as a plastic or a ceramic material. Device 70 is operated by pressing aperture 19 against the skin and energizing quartz flash lamp 54 as disclosed above.

It is noted that many different forms of extender 63 can be made, each having an aperture of a different shape and/or size for adapting device 70 for removing hair from different regions of skin of different organs such as the face the limbs and the like.

Figure 10:
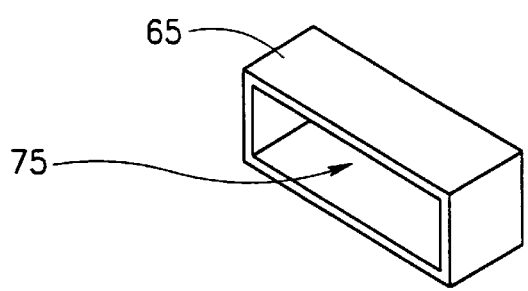
FIGS. 10–12 are schematic isometric views of three differently shaped extenders useful for hair removal when used with the hair removal device of FIG. 9.
Figure 11:
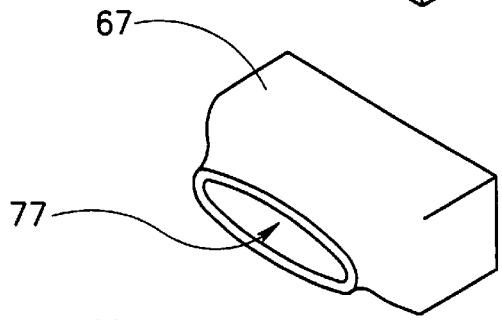
Figure 12:
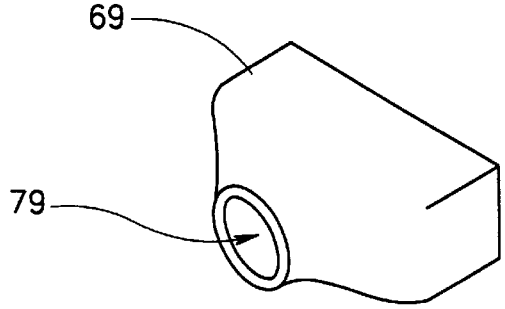

Reference is now made to FIGS. 10–12 which are schematic isometric views of three differently shaped extenders 65, 67 and 69 useful for hair removal when used with the hair removal device 70 of FIG. 9. FIG. 10 illustrates an extender 65 having a rectangular aperture 75. FIG. 11 illustrates an extender 67 having an ellipsoidal aperture 77. FIG. 12 illustrates an extender 69 having a circular aperture 79. Each of extenders 65, 67 and 69 may be used with device 70 for removing hair from various skin regions.

It is noted that, extenders 63, 65,67 and 69 of FIGS. 9–12, respectively, may also include a sealing gasket (not shown) attached to the end of the extender distal from device 70 and made from a soft resilient material such as soft rubber for better sealing of the contact region with the skin. Extenders 63, 65,67 and 69 of FIGS. 9–12, respectively may or may not be internally coated as described above.

In accordance with a preferred embodiment of the present invention, flash lamps 14 and 54 may be disposable to allow convenient replacement of the lamp once it is burnt out.

It is noted that, while the preferred embodiments of the hair removing devices of FIGS. 1–9 have a housing shaped generally as a rectangular open box, other embodiments are possible in which the housing has other shapes such as a cylindrical shape, a triangular prism shaped open box, a truncated triangular prism shaped open box or any other suitable shape having an open side and capable of forming a sealed cavity when suitably placed on the skin.

Figure 13A:
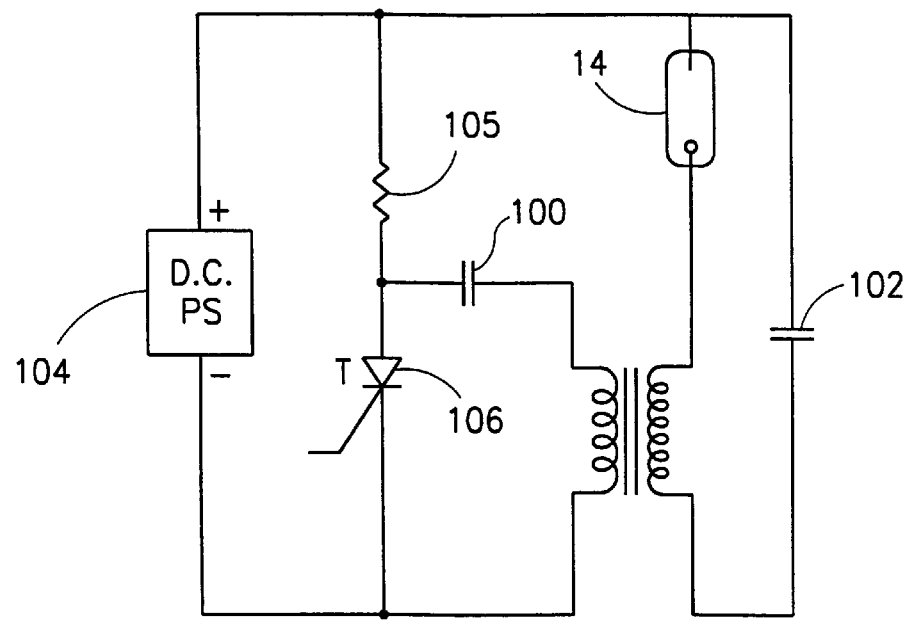
FIGS. 13A and 13B are schematic drawings of excitation circuits and flash tube connections, in accordance with preferred embodiments of the invention.

A preferred embodiment of the assembly 16 as shown in FIG. 13A, comprises two capacitors 100 and 102, a charging resistor 103, a power source 104, a thyristor or other switch 106 and a trigger transformer 108. Such assemblies for energizing flash lamps (and other suitable assemblies) are well known in the art and will not be described further. For example, a suitable flash lamp assembled together with assembly 16 is commercially available from All Electronics Corporation, CA, USA, as flash assemblies under catalog numbers FSH-1 and FSH-4. In the FSH-1 flash assembly, flash lamp 14 is assembled with part of assembly 16 wherein a battery is wired thereto. In the FSH-4 all components are connected to an assembly platform including flash lamp 14 and a battery.

It is noted that, while the above commercially available flash assemblies FSH-1 and FSH-4 can be used to implement the present invention, other suitable commercially available systems can be used or modified to make them suitable for use in the present invention by changing any of their components to control the flow of electrical energy flowing through the flash lamp 14. Alternatively the assembly 16 may be constructed from commercially available electrical and electronic parts and commercially available flash lamps.

For example, an embodiment of the hair removing device of the present invention was constructed by modifying commercially available components. The device was built by modifying a model INSTAFLASH 80 electronic flash unit (for use on Kodak Ek-8 instant cameras), commercially available from SUNPAK CORPORATION, Tokyo, Japan. The electronic assembly for energizing the unit included, inter alia, an electrolytic capacitor having a capacitance of 750 microfarads (rated at 300 Volts). To increase the total charge available for discharging the flash lamp, six additional electrolytic capacitors, each having a nominal capacitance of 410 microfarads (rated at 300 Volts) were electrically connected in parallel with the 750 microfarads capacitor, increasing the total capacitance to a nominal value of 3210 microfarads (rated at 300 Volts).

The original reflector and flash lamp of the flash unit were replaced with a model A1033 flash tube with reflector, commercially available from The Electronic Goldmine, Arizona, USA The flash lamp is 1.75 inches long and the reflector has a rectangular opening having the dimensions of approximately 21 by 44.3 mm. The approximate distance from the center of the flash lamp to the center of the area defined by the opening of the reflector is 14 mm. The reflector is made of a plastic material with a reflective coating. The calculated electrical energy stored by the capacitors of the modified unit is approximately 144 joule. It is estimated that more than 50% of this energy is converted to heat during the flashing of the flash lamp. The modified flash unit was powered by four standard AA size 1.5 volt alkaline batteries or, alternatively, by a commercial 6 volts, 2 amperes DC power supply. Both power sources gave essentially similar results.

The opening of the reflector was placed in contact with the skin of the hand of one of the inventors of the present invention by lightly pressing the reflector against the skin and the flash unit was activated to energize the flash lamp. The reflector was lifted from the skin at about 0.5 seconds after the activation of the flash unit. It was found that lifting of the reflector from the skin at about 0.5 seconds after the activation of the flash lamp unit, results in efficient hair removal while preventing any pain sensation and undue heating of the region of skin 25 which was under the opening. However, It is noted that the optimal time of lifting of the device may vary in different embodiments of the device and may depend, inter alia, on the size and shape of the housing (or reflector), the distance of the flash lamp from the skin, the maximal temperature reached by the flash lamp, the degree of skin pigmentation and the particular region of skin which is being treated.

Figure 13B:
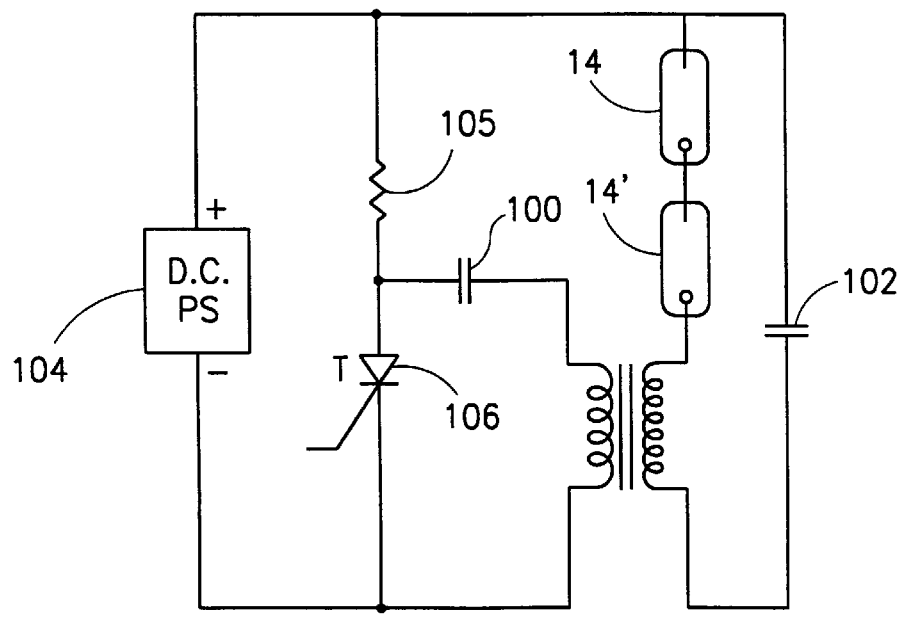

In a preferred embodiment of the invention, as shown in FIG. 13B, a plurality of flash lamps are used, preferably connected in series. This embodiment results in a longer flash time, substantially equal to about twice the flash time when a single tube is used. However, when two tubes are used, the spectrum is shifter toward higher wavelengths and a lower radiation power density at the skin results. The heat generation remains practically the same as when a single tube is used.

It is noted that the devices disclosed herein are only given by way of example and are not intended to limit the scope of the present invention. The structure and dimensions of the devices and the above disclosed parameters for activating and using the devices may be changed and modified according to the desired implementation of the device and may depend, inter alia, on the type and size of the flash lamp, the electrical charge required for pulsing the flash lamp, the type size and reflectivity of the reflector, the dimensions of the opening of the reflector or housing of the device and on the skin pigmentation of the person using the devices. Furthermore, features shown in the various embodiments of the invention may be combined and/or omitted in other embodiments of the invention.

It is further noted that, any of devices for removing hairs 10, 20, 30, 40, 50, 60 and 70 described above may also include a device housing to which the various components of each device are attached. For example, the power assembly 16 and the housing 12 of the device 10 may be attached to a device housing. Similarly, the power assembly 16, the controller 38, the housing 32 and the air pump 34 of the device 30 (FIG. 5), may all be attached to a device housing.

It will be appreciated that device 10, being a hand held, portable device directed for use by the user himself, has a size which allows it to fit into the palm of a hand. However, other preferred embodiments of the present invention are possible which are larger and do not fit in the palm of the hand.

It will be appreciated by the person skilled in the art that the invention is not limited to what has been shown above. While the invention has been described with respect to a limited number of embodiments, it will be appreciated that many variations, modifications and other applications of the invention may be made.

The terms "include" and "comprise" and their conjugations, when used in the claims mean "including, but not necessarily limited to."

What is claimed is:

1. Apparatus for removing hairs from a region of skin, the apparatus comprising:
a housing having an opening therein, the housing forming a cavity enclosing a volume of air when the opening is placed in contact with the region of skin;
a switchable heat source disposed within the housing that rapidly heats the volume of air to a temperature sufficient to destroy the hair by conduction of heat along the length of the hair to a follicle thereof; and
a power source that controllably energizes the heat source.

2. Apparatus according to claim 1 wherein the heat source forms a temperature gradient between the source and the skin.

3. Apparatus according to claim 1 wherein the cavity is a sealed cavity.

4. Apparatus according claim 1 wherein the heat source also provides pulsed light that irradiate the region of skin, the light having an energy insufficient to destroy the hair.

5. Apparatus according to claim 4 wherein the pulsed light is a broad band pulsed light.

6. Apparatus according to claim 4 and including a filter disposed between the heat source and the opening which filters a preselected portion of the pulsed broad band light.

7. Apparatus according to claim 1 wherein the heat source is a flash lamp or an arc discharge lamp.

8. Apparatus according to claim 1 wherein the housing further comprises a sealing gasket attached to the housing along the circumference of the opening.

9. Apparatus according to claim 1 and including a pump having a port communicating with the cavity.

10. Apparatus according to claim 9 and including a controller that energizes the pump to reducing the air pressure within the air cavity to lift at least some of the hairs from the skin.

11. Apparatus according to claim 10 wherein the controller causes energizing of the heat source after lifting at least some of the hair.

12. Apparatus according to claim 9 and including a controller that energizes the pump to exchange air within the cavity at a predetermined time after the heat source is energized.

13. Apparatus according to claim 12 and including at least one valve that allows exchange of air within the cavity when the pump is energized.

14. Apparatus according to claim 13 wherein the at least one valve is at least one one-way valve which allows air to enter the cavity when the pump is activated to draw air from the cavity.

15. Apparatus according to claim 9 wherein the pump pumps air into the cavity at the predetermined time.

16. Apparatus according to claim 1 including a hair aligning member situated at the opening which raises at least some of the hairs from the skin.

17. Apparatus according to claim 16 wherein the hair aligning member is a flat comb-like member or a flat perforated member.

18. Apparatus according to claim 16 wherein the hair aligning member is made of a material which substantially blocks light having a wavelength lower than about 400 nanometers and substantially passes light having a wavelength higher than about 450 nanometers.

19. Apparatus according to claim 1 and including a reflector that reflects light produced by the heat source toward the skin.

20. Apparatus according to claim 19 wherein the reflector substantially absorbs light having a wavelength lower than 400 nanometers.

21. Apparatus according to claim 1 and comprising an extension, the extension having a first end attachable to the opening and a second end placeable on the region of skin, the extension has an aperture therethrough defining an area for removing hairs.

22. Apparatus according to claim 1, which apparatus fits into the palm of a hand.

23. Apparatus for removing hairs from a region of skin, the apparatus comprising:
   a housing having an opening therein, the housing forming a cavity enclosing a volume of air when the opening is placed in contact with the region of skin;
   a switchable energy source disposed within the housing which provides energy in an amount sufficient to destroy at least some of the hairs;
   a power source that controllably energizes the heat source;
   a pump having a port communicating with the cavity; and
   a controller that energizes the pump to reducing the air pressure within the air cavity to lift at least some of the hairs from the skin and that causes energizing of the energy source after lifting at least some of the hair.

24. Apparatus according to claim 23 wherein the controller that energizes the pump to exchange air within the cavity at a predetermined time after the energy source is energized.

25. Apparatus according to claim 24 and including at least one valve that allows exchange of air within the cavity when the pump is energized.

26. Apparatus according to claim 25 wherein the at least one valve is at least one one-way valve which allows air to enter the cavity when the pump is activated to draw air from the cavity.

27. Apparatus according to claim 24 wherein the pump pumps air into the cavity at the predetermined time.

28. A method for removing a plurality of hairs from a region of skin, each of the hairs having a first part disposed in a hair follicle within the skin and a second part distal of the skin, the method comprising:
   irradiating the region of skin with a pulse of light to elevate the temperature of the first part of at least some of the hairs and of hair follicles of the at least some of the hairs to a first temperature, the first temperature being lower than the coagulation temperature of blood;
   then, selectively heating a portion of the second part of at least one of the plurality of hairs; and
   conducting heat from the second part to the hair follicle of the at least one of the plurality of hairs to thereby heat the hair follicle to a temperature high enough to cause the coagulation of the blood vessels supplying blood to the hair follicle.

29. A method according to claim 28 wherein the pulse of light is a broad band pulse of light.

30. A method according to claim 29 wherein the pulse of light is filtered to remove a preselected portion of the pulsed broad band light.

31. A method according to claim 28 and including keeping the temperature of the region of skin away from the hairs below the temperature required to coagulate blood.

32. A method according to claim 28 wherein selectively heating comprises:
   providing a temperature gradient such that air in the vicinity of the second portion of the at least one hair is at a high temperature and air in the vicinity of the skin is below the temperature required to coagulate blood, except for heating of the immediate vicinity of the hair by conduction via the hair.

33. A method according to claim 28 wherein selectively heating comprises flashing a flash lamp or an arc discharge lamp at a distance from the skin.

34. A method according to claim 33 wherein heating comprises providing a pulsed discharge.

35. A method according to claim 33 and including heating the skin and the first part of the hair to a temperature below the coagulation temperature using electromagnetic radiation.

36. A method according to claim 35 wherein heating the skin and the first part of the hair includes filtering the electromagnetic radiation to produce a pulse of non-coherent, narrow band electromagnetic energy.

37. A method according to claim 28 wherein selectively heating comprises:
   providing a cavity overlying the region of skin, the cavity comprising a volume of air having a first end proximal to the region of skin and a second end distal to the region of skin;
   heating the air in the cavity to create a temperature gradient in the volume of air, the temperature gradient having a first temperature at the first end and a second temperature at the second end, the first temperature being lower than the second temperature; and
   maintaining the temperature gradient for a predetermined time interval sufficient for heating at least some of the plurality of hairs extending within the volume of air to a temperature sufficient to remove at least part of at least some of the plurality of hairs, while keeping the first temperature below the coagulation temperature of the region of skin.

38. A method according to claim 37 wherein the air cavity is a sealed air cavity.

39. A method according to claim 37 and including removing heat from the air after maintaining the temperature gradient, so as to keep the temperature of the skin below the coagulation temperature.

40. A method according to claim 39 wherein removing heat comprises, cooling the air in the cavity.

41. A method according to claim 40 wherein cooling the air comprises removing air from the cavity.

42. A method according to claim 37 wherein heating comprises providing a pulsed discharge.

43. A method according to claim 37 and including heating the skin and the first part of the hair to a temperature below the coagulation temperature using electromagnetic radiation.

44. A method according to claim 43 wherein heating the skin and the first part of the hair includes filtering the electromagnetic radiation to produce a pulse of non-coherent, narrow band electromagnetic energy.

45. A method according to claim 37 wherein heating comprises pulsing a flash lamp or an arc discharge lamp.

46. A method for removing hairs from a region of skin, the region of skin having a plurality of hairs, each of the plurality of hairs includes a first part disposed in a hair follicle within the region of skin and a second part distal of the region of skin, the method comprising:

providing a cavity overlying the region of skin, the cavity comprising a volume of air having a first end proximal to the region of skin and a second end distal to the region of skin;

heating the air in the cavity to create a temperature gradient in the volume of air, the temperature gradient having a first temperature at the first end and a second temperature at the second end, the first temperature being lower than the second temperature; and maintaining the temperature gradient for a predetermined time interval sufficient for heating at least some of the plurality of hairs extending within the volume of air to a temperature sufficient to remove at least part of at least some of the plurality of hairs, while keeping the first temperature below the coagulation temperature of the region of skin.

47. A method according to claim 46 wherein the air cavity is a sealed air cavity.

48. A method according to claim 46 and including removing heat from the air after maintaining the temperature gradient, so as to keep the temperature of the skin below the coagulation temperature.

49. A method according to claim 48 wherein removing heat comprises, cooling the air in the cavity.

50. A method according to claim 49 wherein cooling the air comprises removing air from the cavity.

51. A method according to claim 46 wherein heating comprises providing a pulsed discharge.

52. A method according to claim 46 and including heating the skin and the first part of the hair to a temperature below the coagulation temperature using electromagnetic radiation.

53. A method according to claim 52 wherein heating the skin and the first part of the hair includes filtering the electromagnetic radiation to produce a pulse of non-coherent, narrow band electromagnetic energy.

54. A method according to claim 46 wherein heating comprises pulsing a flash lamp or an arc discharge lamp.

55. A method for removing hair from a person comprising:

applying heat from a portable hand held apparatus for hair removal, the apparatus comprising a housing having an opening, a switchable heat source disposed within the housing and a power source for energizing the heat source, characterized in that the heat generates a temperature gradient in an air volume enclosed in a cavity formed by placing the opening on a region of skin, the temperature gradient being suitable for hair removal.

56. A method according to claim 55 wherein the applying of heat is performed by the person on his own skin.

57. A method according to claim 55 further including manually removing the opening of the housing from the region of skin.

58. Apparatus for removing hairs from a region of skin, the apparatus comprising:

a housing having an opening therein, the housing forming a cavity enclosing a volume of air when the opening is placed in contact with the region of skin;

a switchable energy source disposed within the housing which provides energy in an amount sufficient to destroy at least some of the hairs;

a power source that controllably energizes the heat source;

a pump having a port communicating with the cavity; and a controller that energizes the pump to exchange air within the cavity at a predetermined time after the energy source is energized.

59. Apparatus according to claim 58 and including at least one valve that allows exchange of air within the cavity when the pump is energized.

60. Apparatus according to claim 59 wherein the at least one valve is at least one one-way valve which allows air to enter the cavity when the pump is activated to draw air from the cavity.

61. Apparatus according to claim 58 wherein the pump pumps air into the cavity at the predetermined time.

* * * * *